US009592385B2

(12) United States Patent
Kaula et al.

(10) Patent No.: US 9,592,385 B2
(45) Date of Patent: Mar. 14, 2017

(54) PATIENT HANDHELD DEVICE FOR USE WITH A SPINAL CORD STIMULATION SYSTEM

(71) Applicant: Nuvectra Corporation, Plano, TX (US)

(72) Inventors: Norbert Kaula, Arvada, CO (US); Yohannes Iyassu, Denver, CO (US)

(73) Assignee: Nuvectra Corporation, Plano, TX (US)

( * ) Notice: Subject to any disclaimer, the term of this patent is extended or adjusted under 35 U.S.C. 154(b) by 0 days.

(21) Appl. No.: 14/810,758

(22) Filed: Jul. 28, 2015

(65) Prior Publication Data
US 2015/0328463 A1 Nov. 19, 2015

Related U.S. Application Data

(62) Division of application No. 13/118,781, filed on May 31, 2011, now Pat. No. 9,126,043.

(51) Int. Cl.
*A61N 1/36* (2006.01)
(52) U.S. Cl.
CPC ..... *A61N 1/36071* (2013.01); *A61N 1/36132* (2013.01)
(58) Field of Classification Search
CPC ............ A61N 1/36071; A61N 1/36132; A61N 1/37247; A61N 1/36025
See application file for complete search history.

(56) References Cited

U.S. PATENT DOCUMENTS

| 6,587,724 | B2 | 7/2003 | Mann |
| 7,881,805 | B2 | 2/2011 | Bradley et al. |
| 8,762,065 | B2 | 6/2014 | DiLorenzo |
| 8,812,123 | B2 | 8/2014 | Kokones et al. |
| 2006/0058627 | A1 | 3/2006 | Flaherty et al. |
| 2007/0032834 | A1 | 2/2007 | Gliner et al. |
| 2007/0167991 | A1* | 7/2007 | DiLorenzo ......... A61B 5/04001 607/45 |

(Continued)

FOREIGN PATENT DOCUMENTS

WO    WO 03/051175    6/2003

OTHER PUBLICATIONS

European Search Report for Application No. 12169536.5 dated Sep. 28, 2012 (10 pages).

(Continued)

*Primary Examiner* — Catherine Voorhees
(74) *Attorney, Agent, or Firm* — Haynes and Boone, LLP; Eric Li (57) ABSTRACT

A patient feedback device for use in an electrical stimulation system is calibrated. The electrical stimulation system includes an implantable pulse generator (IPG) implanted in a patient and a patient feedback device having a force sensor. Input from the patient is sensed using the patient feedback device. At a first time, an electrical stimulus is applied with the IPG. The force sensor is monitored at a plurality of time points. A level of force sensed by the force sensor at each of the plurality of time points is recorded. A time point at which a maximum force is applied is identified, or a time point at which a minimum force is applied is identified. The first time is compared to the time point at which a minimum force is applied or the time point at which a maximum force is applied, in order to determine a patient response time.

20 Claims, 6 Drawing Sheets

(56) References Cited

U.S. PATENT DOCUMENTS

| | | | |
|---|---|---|---|
| 2008/0269630 A1* | 10/2008 | Denison | A61B 5/0478 600/544 |
| 2009/0018617 A1 | 1/2009 | Skelton et al. | |
| 2009/0105787 A1* | 4/2009 | Kokones | A61N 1/37235 607/59 |
| 2010/0296661 A1* | 11/2010 | Goorevich | H04R 25/505 381/60 |
| 2010/0331921 A1 | 12/2010 | Bornzin et al. | |
| 2011/0093089 A1 | 4/2011 | Martin | |
| 2011/0106198 A1* | 5/2011 | Nakajima | A61B 5/0245 607/17 |
| 2012/0192874 A1 | 8/2012 | Bolea et al. | |
| 2015/0343212 A1* | 12/2015 | Rousso | A61N 1/37247 607/40 |

OTHER PUBLICATIONS

Freescale Semiconductor, Inc. "i.MX51 Applications Processors for Consumer and Industrial Products," Data Sheet: Technical Data, Document No. IMX51CEC, Rev. 4 (Aug. 2010) 200 pages.

North, R.B. et al., "Patient-Interactive, Computer-Controlled Neurological System: Clinical Efficacy in Spinal Cord Stimulator Adjustment" J. Neurosurg. (1992) 76(6): 967-972, http://www.ncbi.nlm.nih.gov.pubmed/1588431.

Texas Instruments Inc., "Mixed Signal Microcontroller," brochure, MSP430G2x32, MSP430G2x02; SLAS723 (Dec. 2010) 53 pages.

Virtualmedicalcentre.com, "Spinal Cord Stimulation Devices," http://www.virtualmedicalcentre.com/devices.asp?sid=2 (Nov. 1, 2008) 7 pages.

* cited by examiner

PATIENT HANDHELD DEVICE FOR USE WITH A SPINAL CORD STIMULATION SYSTEM

PRIORITY DATA

The present application is a divisional application of U.S. patent application Ser. No. 13/118,781, filed on May 31, 2011, the disclosure of which is hereby incorporated by reference in its entirety.

BACKGROUND

The invention relates to a patient handheld device for a stimulation system, such as a spinal cord stimulation (SCS) system, and in particular to a handheld device that a patient can use to provide feedback during programming of an electrical stimulation generator, such as an implantable pulse generator (IPG).

A spinal cord stimulator is a device used to provide electrical stimulation to the spinal cord or spinal nerve neurons for managing pain. The stimulator includes an implanted or external pulse generator and an implanted medical electrical lead having one or more electrodes at a distal location thereof. The pulse generator provides the stimulation through the electrodes via a body portion and connector of the lead. Spinal cord stimulation programming is defined as the discovery of the stimulation electrodes and parameters that provide the best possible pain relief (or paresthesia) for the patient using one or more implanted leads and its attached IPG. The programming is typically achieved by selecting individual electrodes and adjusting the stimulation parameters, such as the shape of the stimulation waveform, amplitude of current in mA (or amplitude of voltage in V), pulse width in microseconds, frequency in Hz, and anodic or cathodic stimulation.

With newer medical electrical leads having an increased number of electrodes, the electrode and parameter combination increases exponentially. This results in a healthcare professional, such as a clinician, requiring a substantial amount of time for establishing a manually created protocol for providing therapeutic spinal cord stimulation. Therefore, a manual approach for creating a protocol is not an optimal solution for the SCS system.

SUMMARY

Numerous embodiments of the invention provide a method and system for programming an SCS system with a substantially reduced time requirement and increased accuracy. More specifically, in numerous embodiments, a sweep process is used with the electrodes of an implanted medical lead to determine the proper SCS program (also referred to herein as an SCS protocol) for providing the best possible pain relief for the patient. In other embodiments, a sweep process can be used on a single electrode by varying a pulse width, frequency, or amplitude applied to the single electrode, for example. It is also envisioned that other sweep processes are possible, such as combinations of the above sweep processes.

Thus, in one aspect the invention provides a patient feedback device for communicating with a programming device of an electrical stimulation system. The device includes a housing, a sensor, a controller, and a communication port. The sensor is supported by the housing and generates a sensor signal in response to an action from the patient. The controller is supported by the housing and is in operative communication with the sensor. The controller receives the sensor signal and sends information to the communication port based on the sensor signal. The communication port is connected to the housing and is in operative communication with the controller. The communication port receives information from the controller and wirelessly transmits a communication signal to the programming device of the electrical stimulation system.

In another aspect the invention provides a method of providing patient feedback to a programming device of an electrical stimulation system with a patient feedback device, where the patient feedback device includes a housing having a sensor, a controller, and a communication port connected thereto and the controller is in operative communication with the sensor and the communication port. The sensor detects a force, a distance traveled, or other impetus applied by the patient in response to a stimulus received by the patient. The sensor generates a signal in response to the applied impetus. The controller receives the signal generated by the sensor. The controller sends information to the communication port based on the signal. The communication port transmits a signal to the programming device.

In still another aspect the invention provides a patient feedback device for communicating with a programming device of an electrical stimulation system. The device includes a resilient housing, a sensor, a controller, and a communication port. The sensor is supported by the housing and generates a sensor signal in response to an impetus applied to the housing by the patient. The controller is supported by the housing and is in operative communication with the sensor. The controller receives the sensor signal and sends information to the communication port based on the sensor signal. The communication port is connected to the housing and is in operative communication with the controller. The communication port receives information from the controller and transmits a communication signal to the programming device of the electrical stimulation system.

In yet another aspect the invention provides a method of calibrating a patient feedback device for use in an electrical stimulation system, where the system includes an implantable pulse generator (IPG) implanted in a patient and a patient feedback device having a force sensor. The method includes steps of: sensing input from the patient using the patient feedback device; at a first time, applying an electrical stimulus with the IPG; monitoring the force sensor at a plurality of time points; recording a level of force sensed by the force sensor at each of the plurality of time points; identifying at least one of a time point at which a maximum force is applied and a time point at which a minimum force is applied; and comparing the first time to at least one of the time point at which a minimum force is applied and the time point at which a maximum force is applied to determine a patient response time.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other constructions and of being practiced or of being carried out in various ways.

The invention herein relates to an electrical stimulation system for providing stimulation to a target tissue of a patient. The electrical stimulation system includes a patient-feedback device (PFD) 145. In the construction shown, the PFD 145 is for use with a spinal cord stimulation (SCS) system 100, which provides electrical pulses to a patient, including to the neurons of the spinal cord and/or sacrum of a patient. Other electrical stimulation systems provide electrical pulses to other portions of a patient's body including a muscle or muscle group, peripheral nerves, the brain, etc.

In various implementations, the PFD 145 is used in conjunction with a clinician programmer (CP) 130 to program an implantable pulse generator (IPG) 115 for a patient. The IPG 115 communicates with any one of the CP 130, a patient programmer and charger (PPC) 135, and a pocket (or fob) programmer (PP) 140. As discussed in further detail below, the CP 130 interacts with the IPG 115 to develop a program (or protocol) for stimulating the patient, which may be facilitated through the use of the PFD 145. Once a protocol is developed by the CP, the PPC 135 or the PP 140 can activate the protocol. The protocol may be stored at the IPG 115 or can be communicated and stored at the PPC 135 or the PP 140. The PPC 135 also is used for charging the IPG 115. Constructions of the IPG 115, CP 130, PPC 135, and PP 140 are disclosed in U.S. patent application Ser. Nos. 13/118,775 (U.S. Pat. Appl. Publ. No. 2012/031300) and Ser. No. 13/118,764 (U.S. Pat. Appl. Publ. No. 2012/031299), both of which are filed on even date herewith and are entitled "SYSTEM AND METHOD OF ESTABLISHING A PROTOCOL FOR PROVIDING ELECTRICAL STIMULATION WITH A STIMULATION SYSTEM TO TREAT A PATIENT", respectively, and both of which are incorporated herein by reference.

Figure 1:
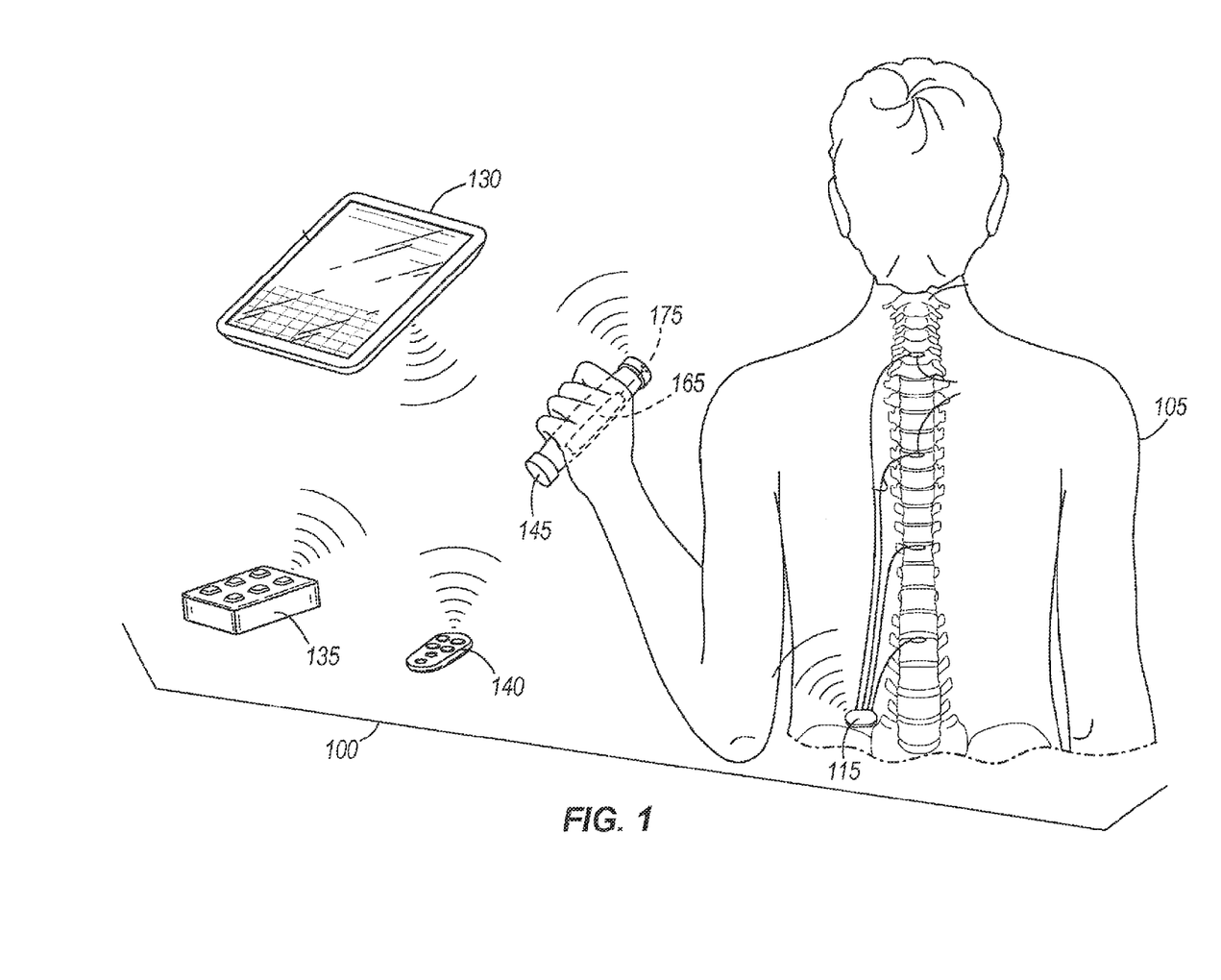
FIG. 1 is a partial perspective view of a patient using a spinal cord stimulation system.

Referring back to FIG. 1, a user may provide feedback to the CP 130 with the PFD 145 while the CP 130 develops the protocol for the IPG 115. In the construction shown in FIG. 1, the PFD 145 is an ergonomic handheld device having a sensor (also referred to as input) 165, a controller, and a communications output 175. The sensor 165 can include a discrete switch and/or a continuously variable input, such as through the use of a thermocouple, strain gauge, pressure sensor, piezoelectric device, accelerometer, displacement mechanism, or other variable sensing mechanism. It is envisioned that the use of a continuously variable input can provide magnitude information, thereby providing improved feedback information from the patient.

In use, the CP 130 activates one or more of the electrodes of the IPG 115 in various patterns. When the patient 105 feels a sensation as a result of a stimulus, such as a stimulus for paresthesia, he or she activates a sensor on the PFD 145. The activation of the sensor indicates to the system 100 that the patient 105 felt the stimulus and can also convey the degree of sensation that is felt, depending on the type of sensor that is employed. Given that there may be a delay from the time the patient 105 feels a sensation and activates the sensor, the system 100 then re-stimulates the most recently-activated combinations of electrodes and the patient 105 again uses the PFD 145 to indicate when (and to what degree) a sensation is felt in order to determine the combination of electrodes to which the patient 105 was reacting. Further description of methods for use of the IPG 115, CP 130, PPC 135, PP 140, and PFD 145 are disclosed in U.S. patent application Ser. Nos. 13/118,775 and 13/118,764, both of which were incorporated by reference above.

Figure 2:
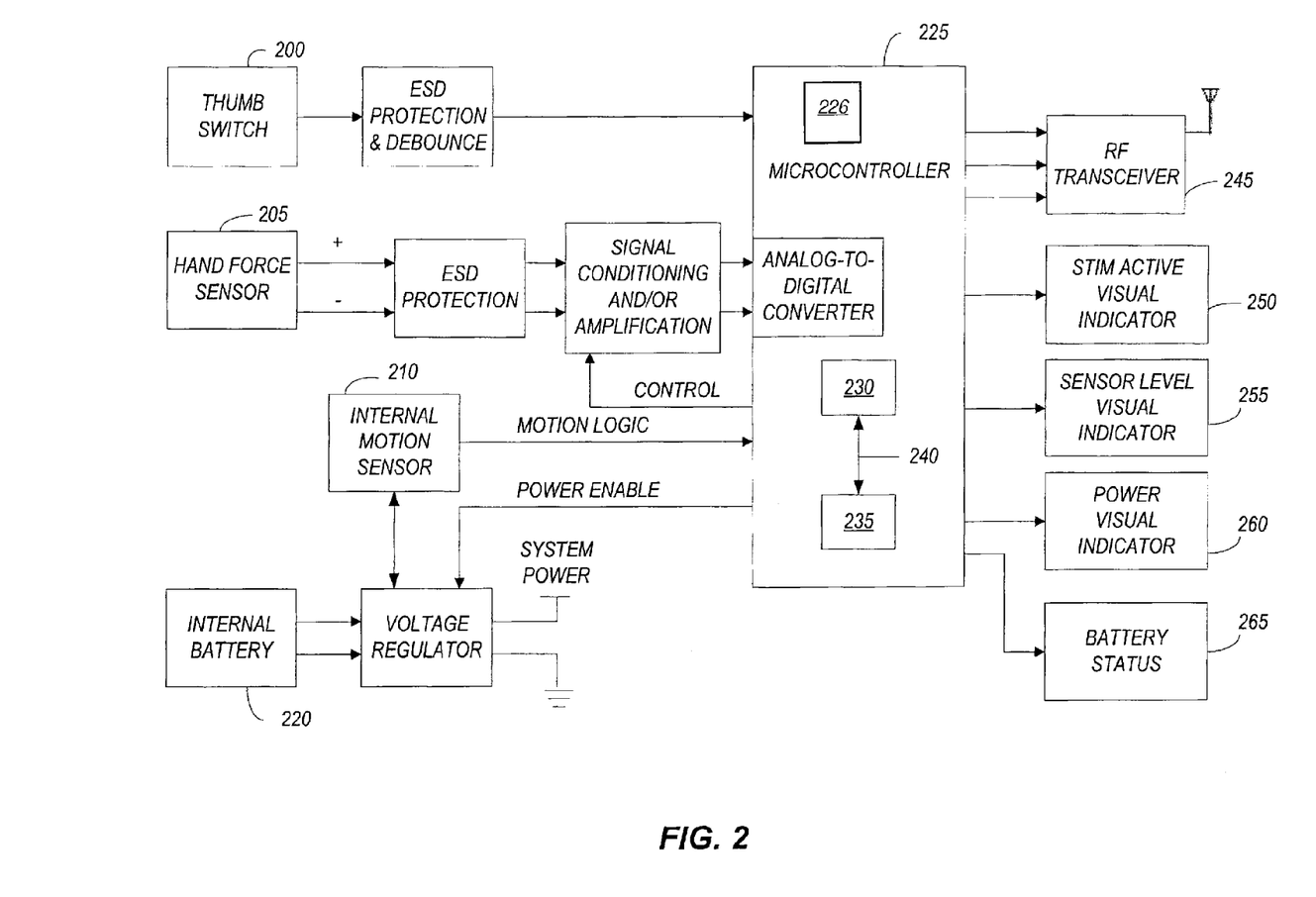
FIG. 2 is a block diagram of a patient-feedback device for use in the spinal cord stimulation system of FIG. 1.

FIG. 2 provides a block diagram of an exemplary hand-held PFD 145 for use in the SCS system 100. In various constructions, the PFD 145 includes a housing 400 which may have one or more of a sensor, a controller, and/or a communication port connected thereto. The construction of the PFD 145 shown in FIG. 2 includes two inputs 200 and 205 in communication with the housing 400 of the device 145 and one input 210 internal to the housing 400. One of the external inputs 200 is a binary ON/OFF switch, preferably activated by the patient's thumb, to allow the patient 105 to immediately deactivate stimulation. Input 200 may be coupled to the controller 225 via electrostatic discharge (ESD) protection and/or debouncing circuits. The second input 205 includes a force sensor sensing the pressure or force exerted by the patient's hand. Input/sensor 205 may be coupled to the controller 225 via ESD protection, signal conditioning, and/or signal amplification circuits. The sensed parameter can be either isotonic (constant force, measuring the distance traversed) or isometric (measured force, proportional to pressure applied by patient 105). The resulting signal from the sensor 205 is analog and, therefore, after the signal is conditioned and/or amplified, it can be passed to microcontroller 225 via an analog-to-digital converter.

The internal input 210 for the PFD 145 of FIG. 2 is a motion sensor. The sensor 210, upon detecting motion, initiates activation of the PFD 145. The device 145 stays active until movement is not detected by the sensor 210 for a time period, which in various constructions may be between one second and five minutes. Power is provided by an internal battery 220 that can be replaceable and/or rechargeable, which in various constructions has an approximately three hour life under continuous use. As discussed below, a motion sensor such as sensor 210 can also be used to obtain feedback from the patient 105 regarding paresthesia.

The processing of the inputs from the sensors 200 and 205 takes place in a controller, such as a microcontroller 225. An exemplary microcontroller capable of being used with the invention is microcontroller 225, which includes a suitable programmable portion 230 (e.g., a microprocessor or a digital signal processor), a memory 235, and a bus 240 or other communication lines. Output data of the microcontroller 225 is sent via a Bluetooth bi-direction radio communication port 245 to the CP 130. The Bluetooth portion 245 includes a Bluetooth communication interface, an antenna switch, and a related antenna, all of which allows wireless communication following the Bluetooth Special Interest Group standard. Other forms of wired and wireless communication between the PFD 145 and other components of the system including the CP 130 are also possible. Other outputs may include indicators (such as light-emitting diodes) for communicating stimulation activity 250, sensor activation 255, device power 260, and battery status 265.

The housing 400 of the PFD 145 may be cylindrical in shape (FIG. 1), and in one particular construction the cylinder is approximately 35 mm in diameter and 80 mm in length. In other constructions the cylinder is larger or smaller in diameter and/or length, for example in order to accommodate hands of varying sizes. In various constructions the diameter can range from 20 to 50 mm and the length from 30 to 120 mm, although other sizes above and below these ranges are also possible.

Furthermore, the shape of the PFD 145 can be other than a circular cross-section, for example oval, square, hexagonal, or other shape. Still further, the cross-section of the PFD 145 can vary along its length, for example being cylindrical in some portions and oval, square, hexagonal or other shape(s) in other portions. In yet other constructions, the PFD 145 has a spherical, toroid, or other shape.

The housing 400 may be made from a resilient material such as rubber or plastic with one or more sensor 205 coupled to or supported by the housing 400. The manner in which the sensor 205 is coupled to the housing 400 depends on the type of sensor that is employed, as discussed below. Thus, when the patient 105 applies a force to the housing 400, the sensor 205 generates a signal that generally is proportional to the degree of force applied. Although the discussion herein mentions the patient 105 using his or her hand to generate force to squeeze the housing 400 of the PFD 145, in various constructions the patient 105 may instead use other body parts, such as the mouth (FIG. 10) or foot (FIG. 12), to generate force. More generally, the patient can generate feedback by a physical action, usually a force applied by the hand or other body part, but the physical action can include other movements, such as movement of the patient's eyes (FIG. 9), head, or hands, to generate a feedback signal. After the signal is generated, it is transmitted from the sensor 205 to the controller 225. The controller 225 processes the signal and, based on one or more such signals from the sensor 205, the controller 225 generates another signal that is to be transmitted to the CP 130. The controller 225 sends the signal to be transmitted to the communication port 245 of the PFD 145 from which it is then transmitted to the CP 130 or other external device. As discussed further below, the signal can be transmitted from the communication port 245 to the CP 130 using various wired or wireless methods of communication.

Figure 3:
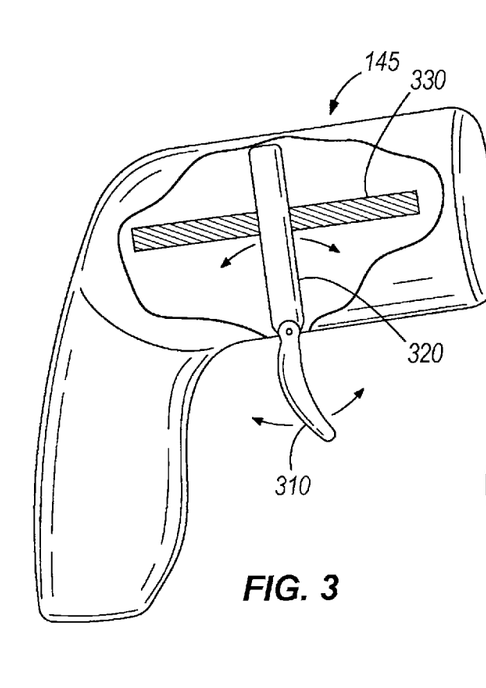
FIG. 3 is a partial cutaway view of a patient feedback device employing an isotonic force sensor.

In various constructions, an isotonic force sensor may include a sensor that measures the distance traveled by the sensor with relatively constant force applied by the patient. Isotonic force sensors may include a trigger 310 (FIG. 3) or other lever mechanism coupled to a wiper 320 that moves along a rheostat 330 or across a series of detectors. Exemplary detectors include electrical contacts or optical detectors, such as photodiodes. In other constructions, an isometric force sensor may include a strain gauge, a piezoelectric device, or a pressure sensor, each of which measures force that is proportional to the pressure applied to the PFD 145 by the patient, generally with only a small amount of travel or shape change to the sensor. Both the isotonic and isometric sensors generate an electrical signal that is proportional to the force that is applied to the sensor. An isometric force sensor may be incorporated into a relatively stiff object such that only slight deformation of the object is needed to register a change in force. In still other constructions, the force sensor may include a combination of elements, such as a trigger or other lever that experiences increasing resistance or pressure as the travel distance increases. For example, increasing resistance or pressure can be created by attaching a relatively stiff spring to the lever or wiper mechanism to increase resistance as the lever or wiper is moved.

Figure 4:
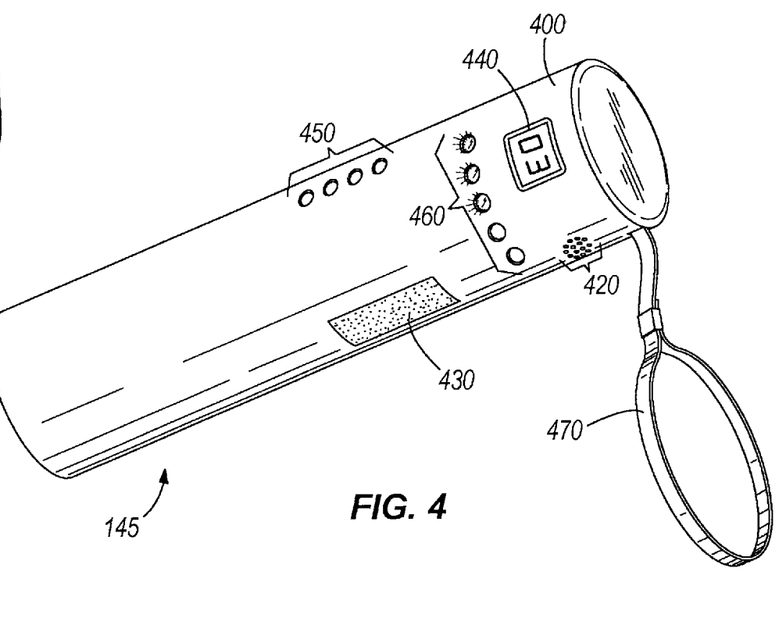
FIG. 4 is a perspective view of a patient feedback device employing an isometric force sensor.
Figure 5:
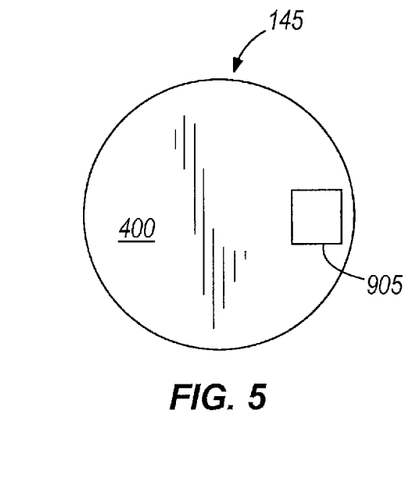
FIG. 5 is a perspective view of a patient feedback device employing a pressure sensor.

In some constructions (e.g. as shown in FIG. 4), the PFD 145 includes a feedback mechanism 460 that indicates to the patient 105 the amount of force that is detected by the force sensor 205. The feedback mechanism 460 may include one or more of a visual, audible, or tactile feedback mechanism that is used to indicate to the patient the degree to which the sensor 205 has been activated, e.g. how much force has been applied or how much the lever or wiper mechanism has traveled. The feedback mechanism gives the patient a sense of whether their activation of the sensor 205 is being detected at what the patient 105 feels is the correct level and to give the patient 105 a means to make their activation of the sensor 205 more consistent. Visual feedback mechanisms 460 can include a series of lights (e.g. LEDs) or a digital readout (e.g. a numerical display); audible feedback can include sounds that vary in amplitude (volume) and/or tone; and tactile feedback mechanisms can include vibration of the PFD 145 and/or altering the shape of the surface of the PFD 145 (e.g. raising of one or more structures such as dots to form Braille-type patterns) in a location that is capable of contacting the patient's skin. Using a combination of feedback modalities will benefit patients who have sensory impairments, including, e.g., impaired hearing and/or sight. The feedback can include a semi-quantitative indication of the patient's response, e.g. including a variety (e.g. 1-5 or 1-10) intensity levels to indicate a relative degree of force applied by the patient. The patient will then be able to see, hear, and/or feel the level of force that is sensed by the sensor 205 of the PFD 145, to help the patient 105 confirm that their response to the stimulus was received, as well as the degree of response that was registered. The correlation between the level of force applied and the output of the feedback device 460 can be calibrated separately for each patient 105 during an initial calibration session.

To facilitate gripping of the PFD 145, the housing 400, in certain constructions, may be covered with one or more surfaces, textures, or materials to improve grip, such as grooves, stipples, indentations, rubber, or plastic, and may include a wrist strap 470 to keep the PFD 145 from falling if it is dropped by the patient.

The PFD 145, in some constructions, may also include a connection feedback mechanism, particularly where the PFD 145 is in wireless communication with the CP 130. The connection feedback mechanism can include one or more of a visual, audible, or tactile mechanism to inform the patient and/or medical personnel of whether the PFD 145 is maintaining a connection with the CP 130, the strength of the connection, and/or if the connection has been lost. For example, the PFD 145 may emit a signal (e.g. light, sound, and/or tactile) at regular (e.g. one minute) intervals to confirm that communication is still maintained. Conversely, the PFD 145 may emit such a signal only if communication is lost. In some constructions, the PFD 145 may tolerate brief intervals in which the signal is lost (e.g. a predetermined time, generally between 0.1-100 sec) before the patient is warned of a possible lost connection. In various constructions, the controller 225 of the PFD 145 includes memory that permits buffering of a limited amount of data, which can be used to accumulate data prior to sending to the CP 130 and which can hold data during brief intervals in which the connection is lost. In various constructions, if communication between the PFD 145 and the CP 130 is lost for more than a predetermined interval of time, then the CP 130 stops stimulation of electrodes until a connection with the PFD 145 is reestablished.

Thus, according to various constructions, the PFD 145 may include one or more of: a sound generating mechanism 420 (e.g. a speaker); a tactile mechanism 430 such as a vibration device and/or a mechanism for creating a raised pattern; a digital numerical readout 440 (e.g. LED or LCD display); and one or more indicator lights 450 (e.g. a series of LEDs); which may be employed to provide feedback to the patient 105 regarding the force being applied and/or communication status.

Various types of sensing mechanisms can be used for the sensor 205, which would depend in part on the type of housing 400 that is used with the PFD 145. For example, if the housing 400 is a sealed, flexible compartment (e.g. a ball or other object filled with gel, air, or liquid) a piezoelectric-based pressure sensing mechanism can be used as the sensor 205 in order to measure changes in pressure when the patient squeezes or relaxes his/her grip on the PFD 145. Alternatively, a rheostat 330 or other linear sensing mechanism can be used with a pistol grip style PFD 145 design (FIG. 3), where a trigger 310 is coupled to a wiper 320 that moves across the rheostat 330 or other linear sensor.

Figure 6:
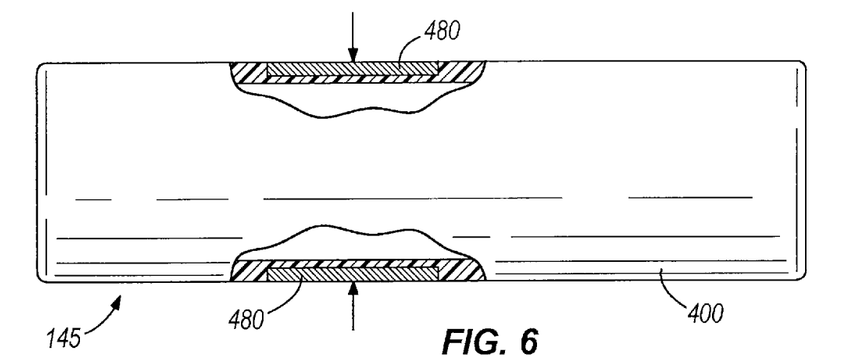
FIG. 6 is a cross-sectional view of a patient feedback device employing strain gauge elements.
Figure 7:
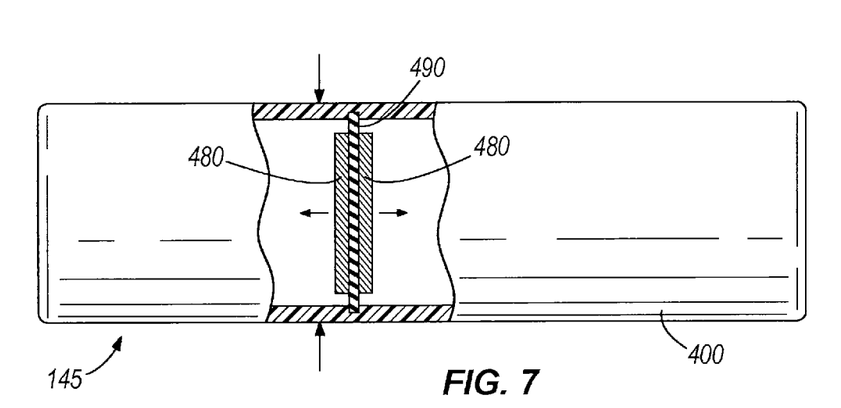
FIG. 7 is a cross-sectional view of a patient feedback device employing strain gauge elements.

In another alternative shown in FIGS. 6 and 7, a strain gauge sensor can be used with a housing 400 that is sufficiently resilient to permit the housing to be deformed so as to activate the strain gauge. The strain gauge elements 480 (e.g. two elements for use with a half-bridge circuit and four elements for use with a full-bridge circuit) can be connected to the housing 400 in several different ways. The elements can be mounted directly to the housing 400, for example on opposing inside flat faces of the housing of the PFD 145, in which case the patient is instructed to squeeze the flat faces towards one another. Alternatively, the strain gauge elements can be mounted to opposite faces of a flexible element 490. The flexible element 490 may be a rectangular strip that is mounted across the inside, for example in a circular shape for mounting inside a cylindrical housing 400. In this particular construction, the flexible element 490 can be mounted inside the housing 400 perpendicular to the outer surface such that applying a force across any opposing sides of the PFD 145 causes the flexible element 490 to flex and thus trigger the strain gauge elements 480. This latter design would remove the requirement for the housing 400 to have opposing flattened faces that the patient would have to squeeze together.

Figure 8:
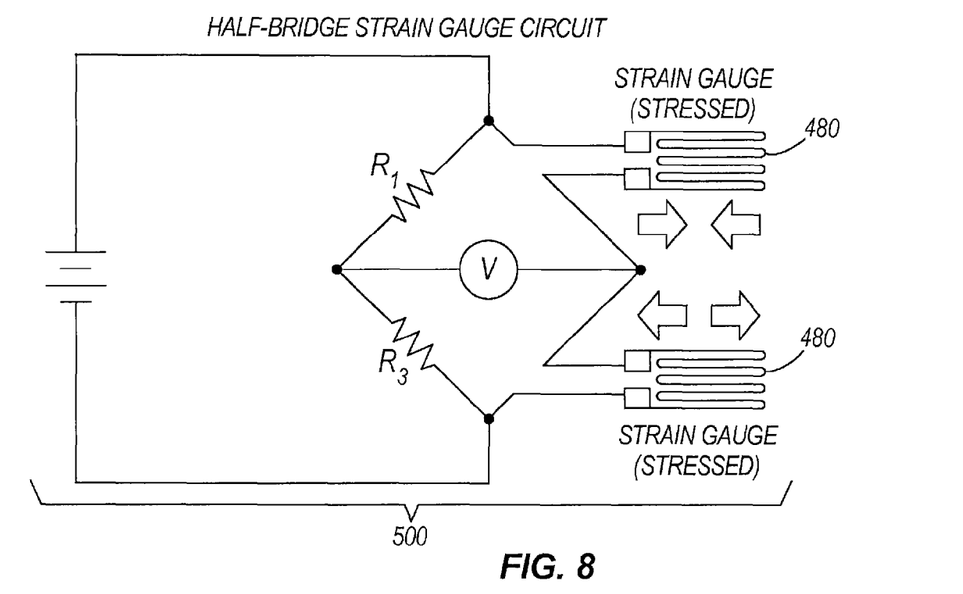
FIG. 8 is a diagram of a half bridge circuit coupled to two strain gauge elements.
Figure 9:
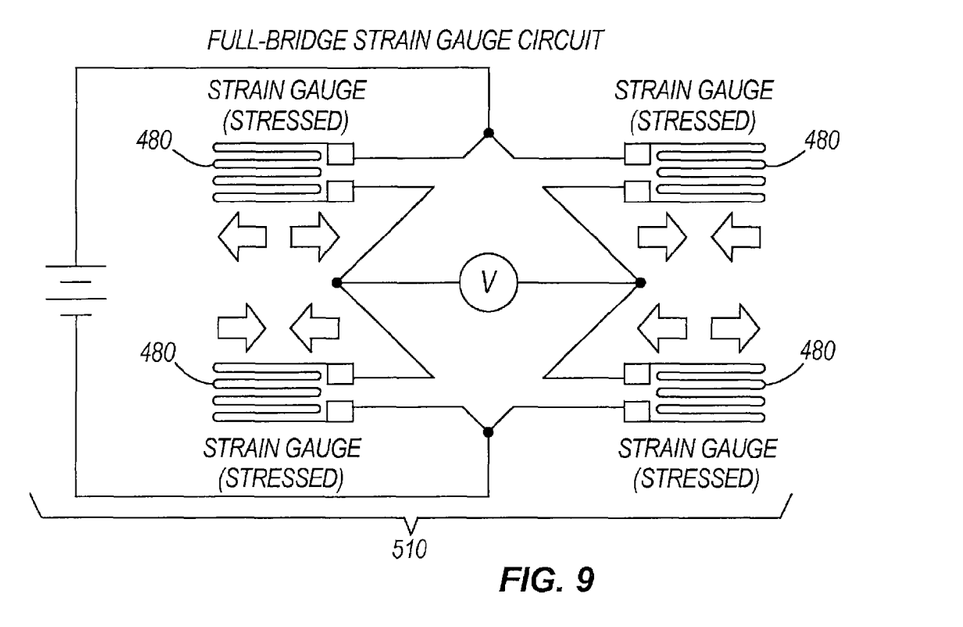
FIG. 9 is a diagram of a full bridge circuit coupled to four strain gauge elements.

In various constructions, two strain gauge elements 480 can be coupled to a half-bridge circuit 500 (FIG. 8), where the use of two elements 480 has the advantage of increasing the signal response as well as canceling out temperature variations in the PFD 145. Alternatively, four strain gauge elements 480 can be coupled to a full-bridge circuit 510 (FIG. 9). As discussed above, the two strain gauge elements 480 can be placed on the inside walls of the housing 400 or can be placed on opposite sites of a flexible element 490 that is mounted inside the housing 400 in a manner that causes the flexible element 490 to bend when a force is applied to the housing 400. The flexible element 490 may be various shapes (e.g. elongated or circular) and more than one flexible element 490 may be mounted inside the housing 400 to enhance the responsiveness of the PFD 145 to applied forces.

Figure 10:
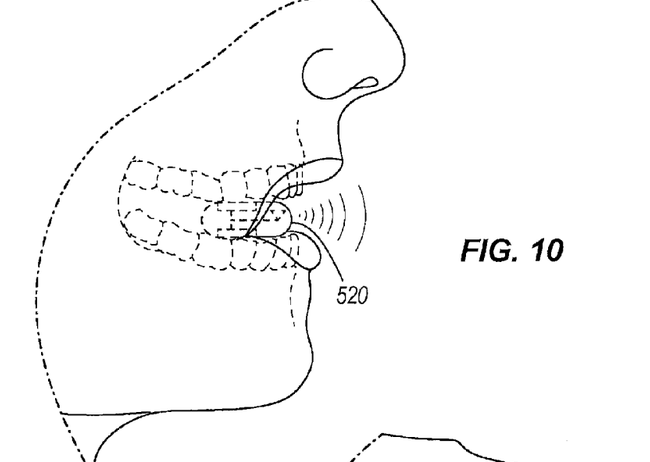
FIG. 10 is a side view of a patient-feedback device inserted in the mouth of a patient.
Figure 11:
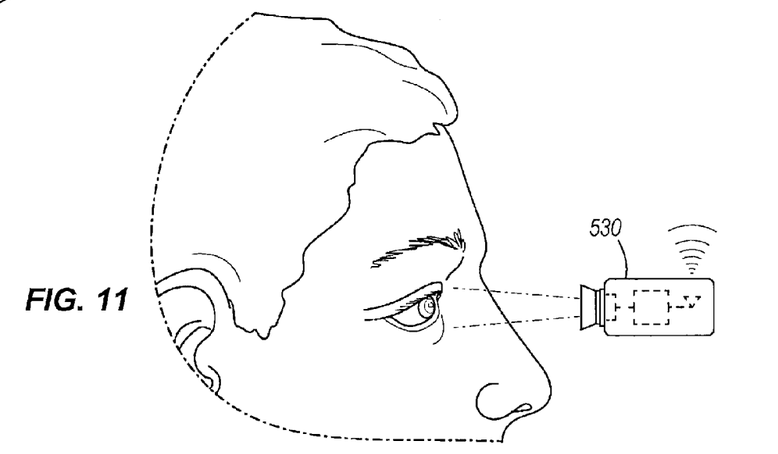
FIG. 11 is a side view of a patient-feedback device with optical sensing.
Figure 12:
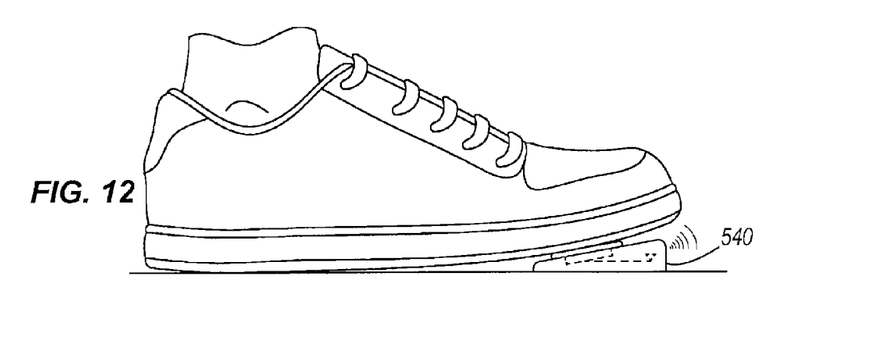
FIG. 12 is a side view of a patient-feedback device activated by a foot of a patient.

FIGS. 10-12 provide other means for receiving patient feedback. More specifically, FIG. 10 shows a mouth-piece 520 that is inserted into the mouth of the patient. The user provides feedback by biting the mouthpiece. FIG. 11 shows an optical sensor 530 (such as a camera and related image processing software) that detects visual cues from a patient. An example visual cue may be the blinking of the patient's eyes. FIG. 12 shows a foot pedal 540 that receives input through the patient's 105 manipulation of a switch and/or sensor with his foot. In other constructions the PFD 145 includes one or more accelerometer (such as the motion sensor 210) and the patient 105 provides feedback by moving the PFD 145 in various distinct patterns that are recognized by the controller 225 of the PFD 145 or by the CP 130. It is also envisioned that the patient may provide feedback directly to the CP 130. In various constructions, the patient 105 is trained to use the particular feedback device (e.g. the PFD 145 or the CP 130 as applicable) in order to properly inform the CP 130 of the patient's reaction to stimuli as they are applied to the IPG 115 in the patient 130. In particular constructions, the CP 130 is programmed to learn the patient's response times and/or the magnitude of the patient's responses in order to obtain a profile of the patient's reaction to various stimuli, as discussed above.

In some constructions the PFD 145 may include a clock (e.g. as part of controller 225) that is synchronized with a clock in CP 130 so that as the patient 105 operates the PFD 145, each action recorded by the PFD 145 has a time associated therewith. Thus, even if there is a delay in transmitting information from the PFD 145 to the CP 130 (e.g. due to communication problems) there will nevertheless be an indication of when each action (e.g. squeezing of the PFD 145 leading to activation of the sensor 205) was recorded, which will enable the CP 130 to determine which of the most recent electrical stimuli likely led to the patient's response.

In some constructions, the PFD 145 can work without calibration in a relative or binary way. However, to facilitate identification of which of the stimuli the patient 105 has reacted to when using the PFD 145, the system 100, in some other constructions, includes procedures for calibrating the patient's response time and/or for 'learning' the patient's response time during ongoing use of the system 100. In one construction, the system 100 includes a calibration procedure in which the patient receives a signal or stimulus to apply pressure to the PFD 145 at time t=0. The actual times that the patient applies and releases pressure (e.g. squeezes the PFD 145 with his or her hand or other body portion) can then be compared and the difference between the signal time at t=0 and the time pressure is applied and released on the PFD 145 are indicators of the patient's response lag time. Knowing the lag time facilitates determining which particular electrical stimulus the patient 105 has responded to via the PFD 145. Although the discussion is presented in terms of the patient applying pressure or force, e.g. with his or her hand, the calibration or learning procedures discussed herein can be applied to other physical actions taken by a patient in response to a signal or stimulus, e.g. movements of the patient's head, eyes, or hands.

Steps of such a calibration procedure for a patient include: at a first time, applying a stimulus to the IPG 115 in the patient; monitoring the sensor 205 of the PFD 145 at a plurality of time points; recording a level of the force sensed by the sensor 205 at each of the plurality of time points;

identifying at least one of a time point at which a maximum force is applied and a time point at which a minimum force is applied; comparing the first time to at least one of the time point at which a minimum force is applied and the time point at which a maximum force is applied to determine a patient response time; and recording the patient response time in a memory.

Analyzing the data generally includes identifying a local minimum or maximum of force, which can be done several ways. One method is to calculate the first derivative (dF/dt) of the force measurements over time to identify the time points at which force is applied (local maximum) and removed (local minimum). Another method is to apply a high-pass filter to the force vs. time data to identify local maxima and minima.

Still another method employs a learning algorithm to identify probabilities of maxima and minima based on the patient's use of the PFD 145. For example, after the patient 105 has squeezed the PFD 145 a number of times in response to electrode stimulation events and the system 100 has identified which stimulation event the patient was responding to, the system 100 can calculate an average lag time from the initial stimulation event to the patient's response thereto.

As discussed further below, the patient 105 provides feedback to the SCS system 100, and specifically the CP 130, while the CP 130 establishes the protocol for the IPG 115. The patient 105 can activate the PFD 145 when the patient 105 feels various stimuli, such as pain (or paresthesia).

Thus, in various constructions the invention provides a useful and novel system and method of providing patient feedback to a programming device of an electrical stimulation system.

What is claimed is:

1. A method of calibrating a patient feedback device for use in an electrical stimulation system, comprising:
    applying an electrical stimulus to a patient;
    measuring, via a force sensor on a patient feedback device, a squeezing of the patient feedback device by the patient in response to the applied electrical stimulus; and
    calculating a patient response time based on a time lag between when the electrical stimulus is applied to the patient and when the patient feedback device was squeezed by the patient in response to the applied electrical stimulus.

2. The method of claim 1, further comprising:
    after the calculating of the patient response time, delivering a plurality of electrical stimuli to the patient;
    detecting a plurality of patient engagements with the patient feedback device in response to the delivering of the plurality of the electric stimuli; and
    determining, based on the calculated patient response time, which of the patient engagements correspond to which of the electrical stimuli, respectively.

3. The method of claim 1, wherein the applying of the electrical stimulus is performed via an implantable pulse generator implanted in the patient.

4. The method of claim 1, wherein the measuring comprises measuring a level of a squeezing force applied by the patient in response to the applied electrical stimulus.

5. The method of claim 4, wherein:
    the measuring of the force comprises:
        monitoring the force sensor at a plurality of time points;
        recording a level of force sensed by the force sensor at each of the plurality of time points; and
        identifying a first time point corresponding to a maximum force and second time point corresponding to a minimum force; and
    the calculating comprises: comparing the first and second time points with a time point when the electrical stimulus was applied.

6. The method of claim 5, wherein the calculating comprises calculating a first derivative of the levels of force sensed by the force sensor at each of the plurality of time points.

7. The method of claim 5, wherein the calculating comprises applying a high-pass filter to the levels of force sensed by the force sensor at each of the plurality of time points.

8. The method of claim 5, wherein the calculating comprises using a learning algorithm to identify probabilities of maxima and minima based on the patient's use of the patient feedback device.

9. The method of claim 1, wherein the patient feedback device includes a motion sensor, and wherein the measuring comprises measuring a movement of the patient as a part of a physical action in response to the applied electrical stimulus.

10. The method of claim 1, wherein the patient feedback device includes an optical sensor, and wherein the measuring comprises measuring visual cues of the patient as a part of a physical action in response to the applied electrical stimulus.

11. A method of calibrating a patient feedback device for use in an electrical stimulation system, comprising:
    delivering a first electrical stimulus to a patient via an implantable pulse generator;
    detecting a first patient engagement with a patient feedback device in response to the first electrical stimulus;
    calculating a patient response time based on a time lag between a first point in time when the first electrical stimulus is delivered and a second point in time when the first patient engagement is detected;
    thereafter delivering a plurality of second electrical stimuli to the patient via the implantable pulse generator;
    detecting a plurality of second patient engagements with the patient feedback device in response to the delivering of the plurality of the second electric stimuli; and
    associating, based on the calculated patient response time, each of the second patient engagements with each of the second electrical stimuli, respectively.

12. The method of claim 11, wherein the patient feedback device includes a force sensor, and wherein the detecting comprises measuring forces applied to the patient feedback device in response to the first electrical stimulus.

13. The method of claim 12, wherein:
    the measuring of the forces comprises:
        monitoring the force sensor at a plurality of time points;
        recording a level of force sensed by the force sensor at each of the plurality of time points; and
        identifying a time point corresponding to a maximum force and a time point corresponding to a minimum force; and
    the calculating comprises: comparing the first point in time with the time points corresponding to the maximum force and the minimum force.

14. The method of claim 13, wherein the calculating comprises one of:
    calculating a first derivative of the levels of force sensed by the force sensor at each of the plurality of time points;

applying a high-pass filter to the levels of force sensed by the force sensor at each of the plurality of time points; or using a learning algorithm to identify probabilities of maxima and minima based on the patient's use of the patient feedback device.

15. The method of claim 11, wherein the patient feedback device includes a motion sensor, and wherein the detecting comprises measuring a movement of the patient in response to the first electrical stimulus.

16. The method of claim 11, wherein the patient feedback device includes an optical sensor, and wherein the detecting comprises measuring visual cues of the patient in response to the first electrical stimulus.

17. A method of calibrating a patient feedback device for use in an electrical stimulation system, the system including an implantable pulse generator (IPG) implanted in a patient and a patient feedback device having a force sensor, the method comprising:

sensing input from the patient using the patient feedback device;

at a first time, applying an electrical stimulus with the IPG;

monitoring the force sensor at a plurality of time points that include a second time point and a third time point;

recording a level of force sensed by the force sensor at each of the plurality of time points;

identifying at least one of: the second time point at which a maximum force is applied and the third time point at which a minimum force is applied; and comparing the first time to at least one of: the second time point and the third time point to determine a patient response time.

18. The method of calibrating a patient feedback device of claim 17, wherein identifying at least one of the second time point and the third time point comprises calculating a first derivative of the levels of force sensed by the force sensor at each of the plurality of time points.

19. The method of calibrating a patient feedback device of claim 17, wherein identifying at least one of the second time point and the third time point comprises applying a high-pass filter to the levels of force sensed by the force sensor at each of the plurality of time points.

20. The method of calibrating a patient feedback device of claim 17, wherein identifying at least one of the second time point and the third time point comprises using a learning algorithm to identify probabilities of maxima and minima based on the patient's use of the patient feedback device.

* * * * *